United States Patent
Richards et al.

(10) Patent No.: US 10,725,038 B2
(45) Date of Patent: Jul. 28, 2020

(54) BIOMARKER SIGNATURES FOR LYME DISEASE DIFFERENTIATION AND METHODS OF USE THEREOF

(71) Applicants: VERAMARX, INC., Boulder, CO (US); Whitney Richards, Boulder, CO (US); Floyd E. Taub, Evergreen, CO (US); Robert A. Rubin, Whittier, CA (US)

(72) Inventors: Whitney Richards, Boulder, CO (US); Floyd E. Taub, Evergreen, CO (US); Robert A. Rubin, Whittier, CA (US)

(73) Assignee: VERAMARX, INC., Boulder, CO (US)

( * ) Notice: Subject to any disclaimer, the term of this patent is extended or adjusted under 35 U.S.C. 154(b) by 0 days.

(21) Appl. No.: 16/068,222

(22) PCT Filed: Jan. 6, 2016

(86) PCT No.: PCT/US2016/012387
§ 371 (c)(1),
(2) Date: Jul. 5, 2018

(87) PCT Pub. No.: WO2017/119881
PCT Pub. Date: Jul. 13, 2017

(65) Prior Publication Data
US 2019/0033310 A1 Jan. 31, 2019

(51) Int. Cl.
*A61K 38/00* (2006.01)
*G01N 33/569* (2006.01)
*G01N 33/68* (2006.01)

(52) U.S. Cl.
CPC ... *G01N 33/56911* (2013.01); *G01N 33/6863* (2013.01); *G01N 2333/20* (2013.01); *G01N 2333/522* (2013.01); *G01N 2800/52* (2013.01); *G01N 2800/60* (2013.01); *Y02A 50/57* (2018.01)

(58) Field of Classification Search
None
See application file for complete search history.

(56) References Cited

U.S. PATENT DOCUMENTS

| | | |
|---|---|---|
| 9,316,652 B2 | 4/2016 | Joosten et al. |
| 10,274,491 B2 | 4/2019 | Richards et al. |
| 2011/0015154 A1 | 1/2011 | Kellermann et al. |
| 2011/0144914 A1 | 6/2011 | Harrington et al. |
| 2013/0115634 A1 | 5/2013 | Mehra et al. |
| 2014/0274925 A1 | 9/2014 | Jin et al. |
| 2015/0141279 A1 | 5/2015 | Walzl et al. |
| 2015/0293096 A1 | 10/2015 | Russell et al. |

FOREIGN PATENT DOCUMENTS

| | | |
|---|---|---|
| WO | WO2011163258 A2 | 12/2011 |
| WO | WO2012039614 A1 | 3/2012 |
| WO | WO 2013110026 | 7/2013 |
| WO | WO 2016007549 | 1/2014 |
| WO | WO 2017119881 | 7/2017 |

OTHER PUBLICATIONS

Li et al (Infect Immun. Jun. 2006;74(6):3305-13).*
Szczepanski et al (Interaction between Borrelia burgdorferi and endothelium in vitro. J Clin Invest. 1990;85:1637-47).*
Aucott et al (Clin. Vaccine Immunol. Sep. 2016. 23(9): 757-766).*
Niddam et al (PNAS | Published online Apr. 10, 2017. E3490-E3498).*
Vechtova et al. Parasites & Vectors (2018) 11:594., pp. 1-27.*
Steere et al (J.Clin Invest. Apr. 2004. 113(8): 1093-1101).*
BD "How to Prepare a Quality Sample" Vacutainer, Retrieved Nov. 7, 2018, 1 page, Retrieved online: www.bd.com/vacutainer/pdfs/VS8876.pdf.
BD "Tech Talk" Retrieved Nov. 7, 2018, 1 page, Retrieved online: www.bd.com/vacutainer/pdfs/techtalk/techtalk_november2005_vs7436.pdf.
CDC "Treatment" Retrieved Nov. 7, 2018, 2 pages, Retrieved online: https://www.cdc.gov/lyme/treatment/index.html.
Cerar et al. "Diagnostic value of cytokines and chemokines in lyme neuroborreliosis." Clin Vaccine Immunol. Oct. 2013;20(10):1578-84.
Extended Search report of related EP 15819031.4, dated Mar. 26, 2018, 12 pages.
Grygorczuk et al., "Concentrations of macrophage inflammatory proteins MIP-1alpha and MIP-1beta and interleukin 8 (il-8) in lyme borreliosis." Infection. Dec. 2004;32(6):350-5.
Hinckley et al., "Lyme disease testing by large commercial laboratories in the United States." Clinical Infectious Diseases. May 2014 59(5):676-81.
Hsu et al., "Differential diagnosis of annular lesions." Am Fam Physician. Jul. 15, 2001;64(2):289-96.
Mayo Clinic "Lyme Disease" Retrieved Jun. 25, 2018, 4 pages, Retrieved online: https://www.mayoclinic.org/diseases-conditions/lyme-disease/diagnosis-treatment/drc-20374655?p=1.
Ilads "Lyme Disease Quick Facts " Retrieved Nov. 7, 2018, 3 pages, Retrieved online: http://www.ilads.org/lyme/lyme-quickfacts.php.
International Search Report of parent PCT/US2015/039436, dated Oct. 6, 2015, 8 pages.
International Search Report of related PCT/US2016/012387, dated Mar. 11, 2016, 10 pages.
Nopper et al., "When it's not ringworm: annular lesions of childhood." Pediatr Ann. Mar. 1998;27(3):136-48.
Soloski et al., "Serum inflammatory mediators as markers of human Lyme disease activity." PLoS One. Apr. 16, 2014;9(4):e93243.

(Continued)

*Primary Examiner* — Jennifer E Graser
(74) *Attorney, Agent, or Firm* — Casimir Jones, S.C.; David Casimir

(57) ABSTRACT

The present invention relates to methods for the differentiating, diagnosing, and treating Lyme disease in a subject. The methods according to the invention are characterized by the detection of a biomarker signature capable of differentiating Lyme disease from like-symptom diseases, the biomarker signature being comprised of a combination of two or more analytes.

15 Claims, No Drawings

(56) References Cited

OTHER PUBLICATIONS

Gautam et al., "Interleukin-10 alters effector functions of multiple genes induced by Borrelia burgdorferi in macrophages to regulate Lyme disease inflammation." Infect Immun. Dec. 2011;79(12):4876-92.

Korwarik et al., "CXCL13 is the major determinant for B cell recruitment to the CSF during neuroinflammation." euroinflammation. May 16, 2012;9:93, 11 pages.

Wang et al. "Pattern of proinflammatory cytokine induction in RAW264.7 mouse macrophages is identical for virulent and attenuated Borrelia burgdorferi." J Immunol. Jun. 15, 2008;180(12):8306-15.

Search Report of related EP Application No. 16884097.3, dated Nov. 25, 2019, 16 pages.

* cited by examiner

BIOMARKER SIGNATURES FOR LYME DISEASE DIFFERENTIATION AND METHODS OF USE THEREOF

FIELD OF THE INVENTION

The present invention relates to the field of medical diagnostics and treatment, and the use of biomarkers in the differentiation of Lyme disease ("LD") infection from other diseases, and more specifically, a LD biomarker signature differentiating LD infection from diseases exhibiting similar symptoms. The present invention relates to a method for differentiating, diagnosing, and treating LD in a subject using the determination of expression levels of at least two, and preferably, a plurality, of biomarkers, e.g., cytokine, chemokine, or other host biochemical.

BACKGROUND OF THE INVENTION

Lyme disease is the most common vector born infectious disease in North America, Asia and Europe. It is a multi-system, inflammatory, progressive disease with a wide range of clinical manifestations, sometimes including erythema migrans ("EM") the initial and readily recognized cutaneous "target" lesion. From EM, which may only present in an estimated 50% of the patients, it may disseminate to other organs, including the nervous system, joints, and heart (http://www.ilads.org/lyme/lyme-quickfacts.php). Such progression may result in permanent neurological and/or musculoskeletal damage, and debilitating symptoms including fatigue and other flu-like symptoms.

A diagnosis of LD is currently based on clinical symptoms and serology, i.e., antibody to LD. The latter may not be detectable during the first few weeks of infection. The current LD diagnosis methodology uses a recommended two-tier serological assay, misses up to 60% of early infections, and is unable to distinguish a past infection from current, active *Borrelia* infection (Hinkley et al, (2014) Clinical Infectious Diseases 59(5):676). More specifically, current sero-diagnostic assays include an ELISA assay to detect antibodies to *Borrelia* species followed by a Western blot for confirmation. If diagnosed in the early stages, the disease can generally be cured with therapeutic agents, e.g., antibiotics. If left untreated, complications involving joints, the heart, and the nervous system can occur. It is therefore crucial to be able to specifically detect and differentiate Lyme disease from other diseases in order to effectively treat it and avoid complications that may develop in later stages. The instant invention includes a method that employs two or more biomatkers to differentiate, diagnose and treat LD.

Due to the fact that few spirochetes are present, i.e., *Borrelia burgdorferi,* the spirochete that causes LD, especially in blood specimens, the best current methods measure immune response. While not fully reviewed here, many steps, including antigen capture by "professional antigen presenting cells" and numerous signaling and processing steps, as well as coordination of various immune cell types, are required prior to production of Ab. For example, prior to Ab secretion numerous immune signaling agents must be secreted and transported from one type of immune cell to another. An immune network including APCs, T-cells of various types and B-cells is generated. Even once these signals are generated numerous steps of B-cell maturation, transcription, translation, processing and secretion are required before even low levels of IgM Ab are present in the blood. Evolution has driven the spirochete to attempt to evade and suppress the Ab response, and numerous steps between the APC and the Ab provide many possible opportunities for suppression. Certain subjects, i.e., genotypes, may also be less effective in promptly completing the process and producing high levels of Ab. Thus, measurement of the earliest steps of immune response, prior to antibody excess that can be measured in the blood, is rationally expected to a more sensitive method of differentiating LD from other diseases.

Although the Ab response may be delayed or weak, a significant number of acute Lyme disease patients have such a florid early immune response that it may be visible with the naked eye as erythema migrans (EM). It is known that some clinicians may miss EM, and some skin types may not show the response. Further, it should be noted that EM detected clinically may not be indicative of Lyme disease. For examples of descriptions and differential diagnosis based on apparent EM, see, e.g., Hsu (2001) Am Fain Physician 64(2):289; and, Nopper (1998) Pediatr Ann 27:136. Other symptoms of initial Lyme disease including, fever, malaise, arthralgia, headache and stiff neck are even less specific than EM.

Currently, there is no accurate way to differentiate other than process of elimination or differential diagnosis methodologies, i.e., epidemiology based or likelihood-ratio based methods.

The signs and symptoms of Lyme disease, other than EM, are non-specific, they may include fever, malaise, body aches, joint pain, neck pain, headache and sore throat. Since EM is present in only the minority of the cases, the clinical diagnosis is very unreliable. While there are specific diagnostic tests for some of the other diseases that cause similar symptoms it is often difficult or impossible to determine what is causing the problem. For example tests for strep throat may be done by a physician on site but they are unreliable. Laboratory tests for other viruses or bacterial infections are possible, however a number of tests would need to be ordered and the results are of variable quality. Further not all the possible items in a differential diagnosis can be easily tested for. As an example cancer is in the differential diagnosis as a common cause of fatigue and it is very difficult to test for all possible causes of cancer; even if a large number of very expensive and time consuming scans are done early cancers are still often missed. Most importantly Lyme disease would still remain a diagnosis of exclusion. In order to definitively separate Lyme disease from other diseases, accurately, in a reasonable period of time and with high specificity a specific diagnostic test is needed.

The significant disadvantages (poor sensitivity and specificity) of current assays lead to a significant medical need for better diagnostic tests for differentiating, diagnosing, and treating Lyme disease. There are some methods that culture blood cells and look for cytokine production in response to antigens for the detection of LD, however these are expensive, labor intensive, rely on artful methods, and require living white blood cells. Molecular proteomic methods of identifying the immune mediators of an early immune response, even when the presenting symptoms are substantially similar to a number of other diseases and/or infections, are targeted in the present invention. These molecular methods are more sensitive and accurate than clinical observation for the purpose of differential diagnosis and precede the presence of positive serology.

A differential diagnosis is typically defined as diagnostic procedures used for distinguishing a disease or condition from others that present similar symptoms. Such procedures are used to diagnose a specific disease and/or eliminate conditions. More specifically, differential diagnostic procedures are systematic diagnostic methods used to identify the presence of a disease where multiple alternatives are possible, wherein a process of elimination is employed that reduces the probability of possible conditions. Historically, evidence such as symptoms, patient history, and medical knowledge and experience are utilized. To date there is not an accurate and effective molecular format for differential diagnosis of LD.

LD is difficult to diagnose because there are myriad conditions and syndromes that have overlapping symptoms, for example, Amyotrophic Lateral Sclerosis, Chronic Fatigue Syndrome, Fibromyalgia, Leptospirosis, Multiple Sclerosis, Rheumatoid. Arthritis, viral infection including flu and colds, bacterial infection, spider bites, skin lesions, etc. Some of these, such as Chronic Fatigue Syndrome, are themselves diagnoses of exclusion for which no tests are available. While many of these conditions might be ruled out via the inefficient diagnostic process of elimination, there remains a need for differentiation and/or diagnosis and/or treatment of LD via molecular methods, and specifically via biomarker signatures capable of differentiating LD from other diseases. In addition to differentiating LD from other diseases, identification of an immune biomarker signature that differentiates LD may also aid in identification of key immunologic pathways that may be targeted for therapeutic purposes. More specifically, biomarker analysis can provide prognostic as well as diagnostic information, guide initial treatment choice, monitor treatment efficacy, and improve outcomes. The two or more biomarkers, hereinafter referred to as the biomarker signature, of the instant invention allow specifically for differentiation from other diseases, disease diagnosis, effective treatment, and progression prevention. Differentiation, diagnosis, appropriate treatment, and prevention of progression and/or recurrence can play a role in all of these disease management areas. The poor sensitivity and specificity of the current methods for detecting LD means that methods for the diagnosing, prognosing, monitoring, differentiating, treating, and managing of Lyme disease in a subject characterized by the detection of a biomarker signature comprised of a combination of two or more analytes differentiating LD from other diseases presenting similar symptoms would be an invaluable tool to aid clinicians. Such methods have the potential to expedite and increase the accuracy of LD diagnosis and treatment.

A method such as discussed herein, that uses, for example, serum, plasma, blood, blood spots, blood filtrate, urine, saliva or tears, to detect the in vivo production of a biomarker signature, i.e., cytokine or other analyte markers, would be easier, more generally applicable, and more accurate than those currently available. Both highly specific and more sensitive tests detecting biomarker signatures may also have value as a component of a multi-tier LD assay. Such a biomarker assay would be more sensitive and more specific than current serological assays, and would provide detection, differentiation, and diagnosis at early time points, i.e., earlier than detection of antibodies. The present invention is an effective diagnostic method for differentiation of LD from other diseases exhibiting similar symptoms, e.g., bacterial, viral, autoimmune, that improves disease outcomes in patients.

SUMMARY OF THE INVENTION

To overcome the low rates of success using the current 2-tier serologic methodology and subsequent treatment, provided herein, are methods for distinguishing, diagnosing, and treating LD, wherein the presence of the biomarker signature is indicative of LD as opposed to other diseases. Said method includes detection of a biomarker signature, said biomarker signature comprises a combination of two or more biomarkers selected from a discrete group of biomarkers, the group comprising Eotaxin, IFN.ganama, SDF.1a.B, EN/X.78, Fractalkine, IL.4, IL 1 b, IL.6, CTACK, SAP, I.309, TECK, MCP.3, PDGF.B, IL.8, BCA.1, SCYB16, GCP.2, MCP.2, MCP.4, MIP.3b, TNF.a, Ferritin, Procalcitonin, 6Ckine, MIP.3a, MPIF.1, a.2.macroglobulin, MIG, and TPA. Biomarker signatures create a "fingerprint" to differentiate, diagnose, and treat a subject.

According to the present invention, provided are biomarker signatures and related methods for distinguishing LD from other diseases, and providing an appropriate treatment based thereon. The present invention, therefore, provides a method of differentiating, diagnosing and treating a subject suspected of LD infection. The present invention provides a method of diagnosing and treating LD in a subject comprising the steps of:

obtaining a sample from the subject;
detecting in the sample the presence of a biomarker signature; and
administering a therapeutic treatment to the subject based on the biomarker signature detection result that differentially diagnoses LD from other diseases.

In some embodiments, detecting the presence of the biomarker signature comprises generating separate complexes between at least one detection agent and two or more analytes.

In some embodiments, the biomarker signature comprises a combination of two or more analytes comprising cytokines, chemokines, prostaglandins, immune response markers, complement components, or host response factors. In some embodiments, the two or more analytes are selected from the group consisting of Eotaxin, IFN.gamma, SDE1a.B, ENA.78, Fractalkine, IL.4, IL.1b, IL.6, CTACK, SAP, I.309, TECK, MCP.3, PDGF.B, IL.8, BCA.1, SCYB16, GCP.2, MCP.2, MCP.4, MIP.3b, TNF.a, Ferritin, Procalcitonin, 6Ckine, MIP.3a, MPIF.1, a.2.macroglobulin, MIG, and TPA. In some embodiments, the two or more analytes are selected from the group consisting of PDGF.B, IL.8, BCA.1, SCYB16, GCP.2, MCP.2, MCP.4, MIP.3b, TNF.a, Ferritin, Procalcitonin, 6Ckine, MIP.3a, MPIF.1, a.2.macroglobulin, MIG, and TPA, or Eotaxin, IFN.gamma, SDF.1a.B, ENA.78, Fractalkine, IL.4, IL.1b, IL.6, CTACK, SAP, I.309, TECK, and MCP.3.

In some embodiments, the two or more analytes are selected from the group consisting of Eotaxin, IFN.gamma, SDF.1a.B, ENA.78, Fractalkine, IL.1b, IL.6, CTACK, SAP, I.309, TECK, MCP.3, PDGF.B, IL.8, BCA.1, SCYB16, GCP.2, MCP.2, MCP.4, MIP.3b, TNF.a, Ferritin, Procalcitonin, 6Ckine, MIP.3a, MPIF.1, a.2.macroglobulin, MIG, and TPA, and at least one additional biomarker selected from the group consisting of TRAIL, B.NGF, IL.10, IL.2, MIP.1d, VEGF, MCP.1., IL.5, Gro.a, IL.16, IP.10, MDC, MIP.1a, MIP.1B, CRP, MIF, Eotaxin.2, Eotaxin.3, GM.CSF, Gro.B, I.TAC, and TARC. In some embodiments, the two or more analytes are selected from the group consisting of PDGF.B, IL.8, BCA.1, SCYB16, GCP.2, MCP.2, MCP.4, MIP.3b, TNF.a, Ferritin, Procalcitonin, 6Ckine, MIP.3a, MPIF.1, a.2.macroglobulin, MIG, and TPA and at least one additional biomarker selected from the group consisting of TRAIL, B.NGF, IL.10, IL.2, MIP.1d, VEGF, MCP.1, IL.5, Gro.a, IL.16, IP.10, MDC, MIP.1a, MIP.1B, CRP, MIF, Eotaxin.2, Eotaxin.3, GM.CSF, Gro.B, I.TAC, and TARC. In some embodiments, the two or more analytes are selected from the group consisting of Eotaxin, IFN.gamma, SDR1a.B, ENA.78, Fractalkine, IL.4, IL.1b, IL.6, CTACK, SAP, I.309, TECK, and MCP.3, and at least one additional biomarker selected from the group consisting of TRAIL, B.NGF, IL.10, IL.2, MIP.1d, VEGF. MCP.1, IL.5, Gro.a, IL.16, IP.10, MDC, MIP.1a, MIP.1B, CRP, MIF, Eotaxin.2, Eotaxin.3, GM.CSF, Gro.B, I.TAC, and TARC.

In some embodiments, an output value biomarker signature score is derived using a statistical algorithm or algorithms to produce a score being indicative of the probability the subject has Lyme disease versus some other disease or no disease at all.

In some embodiments, a method of differentiating, diagnosing and treating a subject suspected of Lyme disease infection, comprising the steps of: obtaining a sample from the subject; detecting in the sample the presence of a biomarker signature distinguishing LD from other diseases; translating the presence of a biomarker signature into an output value biomarker signature score, wherein the output value score is derived using a statistical algorithm or algorithms, the score being indicative of the probability of the subject having Lyme disease; determining Lyme disease status based on the biomarker signature output value score; and administering an appropriate therapeutic treatment to the subject based in part on the resulting biomarker signature output value score.

In another embodiment, a method is for treating Lyme disease in a subject is provided, which comprises the steps of requesting an assay of a sample obtained from a subject, said assay capable of determining a biomarker signature distinguishing Lyme disease from other diseases and indicative of Lyme disease, wherein said biomarker signature comprises two or more analytes; and administering therapeutic treatment to the subject if the results indicate the presence of Lyme disease.

Another embodiment encompasses a method for determining the need for treatment of Lyme disease in a subject, comprising the steps of: performing an assay of a sample obtained from a subject to determine results indicating the presence of a biomarker signature distinguishing Lyme disease from other diseases and indicative of Lyme disease, and providing the results of the assay indicating the presence or absence of the biomarker signature. Some embodiments may further comprise the determination of a score.

In some embodiments, a method for determining the need for treatment of Lyme disease in a subject comprising the steps of: analyzing assay results of an assay indicating whether or not a subject sample has a biomarker signature distinguishing Lyme disease from other diseases and indicative of Lyme disease infection, and administering therapeutic treatment to the subject for Lyme disease based on the assay results.

In some embodiments, a method of identifying a subject suspected of Lyme disease infection as being likely to benefit from therapeutic treatment or not likely to benefit from therapeutic treatment, comprising the steps of: determining analyte concentrations comprising a biomarker signature in a sample obtained from the subject, inputting analyte concentration values into a statistical algorithm or algorithms to produce an output value score indicative of the probability the subject has Lyme disease, wherein a score indicative of the probability of having Lyme disease is indicative of the subject being likely to benefit from treatment. Patients treated with appropriate antibiotics in the early stages of Lyme disease usually recover rapidly and completely. Antibiotics commonly used for oral treatment include doxycycline, amoxicillin, or cefuroxime axetil. Patients with certain neurological or cardiac forms of illness may require intravenous treatment with drugs such as ceftriaxone or penicillin (http://www.cdc.gov/lyme/treatment/index.html).

Another embodiment includes a kit for performing an assay diagnosing Lyme disease comprising: a substrate comprising at least one probe for each of the two or more corresponding analytes selected from the group consisting of a.2.macroglobulin, MIG, BCA.1, Eotaxin, Eotaxin.3, I.TAC, MPIF.1, Procalcitonin, SCYB16, CTACK, MCP.4, TNF.a, GCP.2, MCP.2, MIP.3b, SDF.1a.B, MIP.3a, IFN.gamma, TPA, Fractalkine, ENA.78, IL. 1 b, IL.6, IL.4, SAP, I.309, CTACK, TECK, and MCP.3; and instructions for performing the diagnostic assay.

A biomarker signature is defined by a combination of two or more biomarkers (a.k.a., analytes) and is indicative of the relative likelihood of infection, and in turn, the likelihood of response to treatment. A biomarker may be, e.g., a cytokine, a chemokine, prostaglandin, immune response markers, complement component, or a host response protein or non-protein factor.

In some embodiments, a biomarker signature comprises a combination of two or more biomarkers selected from the group consisting of Eotaxin, IFN.gamma, SDF.1a.B, ENA.78, Fractalkine, IL.4, IL.1b, IL.6, CTACK, SAP, I.309, TECK, MCP.3, PDGF.B, IL.8, BCA.1, SCYB16, GCP.2, MCP.2, MCP.4, MIP.3b, TNF.a, Ferritin, Procalcitonin, 6Ckine, MIP.3a, MPIF.1, a.2.macroglobulin, MIG, and TPA.

In some embodiments, the method further comprises determining a biomarker signature score that is indicative of the likelihood (probability) of the presence or absence of LD versus some other disease presenting similar symptoms, or no disease at all.

In some embodiments, the present invention biomarker signature score may be combined with evidence of the LD spirochete obtained from other bodily fluids or cells including urine, blood, tears, saliva, or WBCs by physical methods such as mass spectrometry, biochemical methods such as polymerase chain reaction, or biological methods such as antibody production in vivo or antibody detection of trapped antigens in order to differentiate LD from other diseases presenting similar symptoms.

In some embodiments, the present invention biomarker signature score is combined with the above LD evidence, and further combined with the production of biomarkers in vitro.

The present invention may include an assay, and/or a kit, and/or a set of reagents for differentiating and diagnosing LD from other diseases in a subject comprising: at least one probe or pair of reagents, which may include antibodies, aptamers or other biomarker binding materials, and beads or plates or other substrates or homogeneous (non-solid substrate) binding reactions for the detection of one or a combination of two or more biomarkers, wherein some embodiments of said biomarkers are selected from the group consisting of Eotaxin, IFN.gamma, SDF.1a,B, ENA.78, Fractalkine, IL.4, IL.1b, IL.6, CTACK, SAP, I.309, TECK, MCP.3, PDGEF.B, IL.8, BCA.1, SCYB16, GCP.2, MCP.2, MCP.4, MIP.3b, TNF.a, Ferritin, Procalcitonin, 6Ckine, MPIF.1, a.2.macroglobulin, MIG, and TPA. In certain embodiments, the kit further includes agents that generate detectable signals, such as, light, absorption of light, fluorescence, enzyme reactions, electrochemical changes, plasmon resonance, magnetic signals, interference patterns or other signals known in the art. In certain embodiments, the substrate may be a glass slide and the apparatus may comprise a microarray. Some embodiments use homogeneous assays that include fluorescent quenching or other methods know in the art. Some embodiments use precipitation or other methods know in the art to measure the binding of a molecular probe to a biomarker. In some embodiments the binding of the biomarker to such a probe on a specialized surface changes the electric, physical or optical properties of that surface allowing detection of the binding event. The binding may be increased by addition, simultaneously or subsequently, of a second reagent, which may also contain easily detectable signal generators known in the art. In some embodiments biomarkers are detected simultaneously in "multiplexed" assays.

DETAILED DESCRIPTION OF THE INVENTION

The present invention relates to biomarker signature based methods for the differentiating, diagnosing, and treating of Lyme disease in a subject, wherein a biomarker signature is comprised of a combination of two or more analytes.

Biomarkers

A biomarker is a biological indicator from a subject, that individually, or more likely in combination with other biomarkers, reflects the absence, presence, or the condition of a disease and/or especially the host response to that disease. Biomarkers may reflect a variety of disease characteristics, including the level of exposure to an environmental or genetic trigger, an element of the disease process itself, and intermediate stage between exposure and disease onset, or an independent factor associated with the disease state, but not causative of pathogenesis. Biomarkers may be used to determine the status of a subject or the effectiveness of a treatment. Biomarker combinations with the most diagnostic utility have both high sensitivity and specificity. In practice, biomarkers and/or specific combinations of biomarkers having both high sensitivity and specificity are not obvious. Evaluation, assessment, and combination of specific biomarkers for diagnosis provide an improved approach to disease treatment.

Biomarker Examples: Cytokines, Acute Phase Reactants, and Complement Factors

Cytokines, prostaglandins, acute phase reactants, and complement factors are examples of biomarkers indicative of a subject's response to infection, immune responses, inflammation, and trauma. Cytokines include, for example, chemokines, interferons, interleukins, lymphokines, and other immune signaling molecules. Biomarker is, for purposes of this application, defined as a measurable substance in a sample from a subject, whose level is indicative of some phenomenon such as normal biologic processes, pathogenic processes, disease, infection, exposure, or response. Biomarkers include, e.g., cytokines, immune response markers, chemokines, complement components, and/or other circulating host factors regulated by the immune system.

Therefore, this invention has identified biomarker signatures that enable a differentiation between LD and other diseases with similar symptoms, and further enables identifying subjects likely to respond to treatment. It has been determined that, contrary to the fact that a biomarker may have virtually no predictive value alone, in combination, biomarkers identified as a signature carry great utility as derived, "secondary" biomarkers wherein the information is provided based on combination. Biomarker signatures that may be relevant to disease diagnosis and treatment, include a combination of two or more, preferably 4-8, and more preferably 9-12 biomarkers chosen from the group consisting of 4-1BB, A-2-macroglobulin, ACE-2, ActivinA, Adiponectin, A.diposin, AgRP, ALCAM, Alpha-fetoprotein, Amphiregulin, Angiogenin, Angiopoietin 1, Angiopoietin 2, Angiostatin, ANGPTL4, Aβ40, Aβ42, Ax1, B7-1(CD80), BCA-1, BCAM, BCMA, BDNF, beta IG-H3, beta-NGF, CA19-9, Carbonic Anhydrase IX, Cardiotrophin-1, CathepsinS, CCL1/I-309, CCL14/HCC-1/HCC-3, CCL14a, CCL14/mip-1 delta/LKN-1, CCL17/TARC, CCL18/PARC, CCL19/MIP3B, CCL20/MIP-3 alpha, CCL21/6Ckine, CCL22/MDC, CCL26/Eotaxin-3, CCL28, CCL3/CCL4 (MIP-1 ALPHA/MIP-1 beta), CD14, CD23, CD30, CD40, CD40 Ligand, CEA, CEACAM-1, Chemerin, CKb8-1, CNTF, C-peptide, Cripto, CRP, CTACK, CX3CL1/Fractalkine, CXCL12/SDF-1, CXCL13, CXCL16, CXCL17/VCC-1, CXCL4/PF4, CXCLS/ENA-78, CXCL7/NAP-2, DAN, Decorin, DKK-1, Dkk-3, Dkk-4, DPPIV, DR6 (TNFRSF21), Dtk, E-Cadherin, EDA-A2, EGF, EGFR, EG-VEGF, Endoglin, Eotaxin, Eotaxin-2, EpCAM, ErbB2, ErbB3, Erythropoietin R, E-Selectin, Fas Ligand, Fas/TNFRSF6, Fc gamma RIM/C, Ferritin, FGF basic, FGF-4, FGF-7, FGF-9, Fibrinogen, FLRG, Flt-3 Ligand, Follistatin, FSH, Furin, Galectin-7, GCP-2, GDF-15, GDNF, GITR, GITR-Ligand, GM-CSF, GRO, GRO-a, GRO-b, Growth Hormone, HB-EGF, HCC-4, hCG intact, HGF, HVEM, I.309, ICAM-1, ICAM-2, ICAM-3, IFN-a2, IFN-g, IFNα, IGF-1, IGF-1sR, IGF-2, IGFBP-1, IGFBP-2, IGFBP-3, IGFBP-4, IGFBP-6, IL-10, IL-10R alpha, 1L-10R beta, IL-11, IL12/1L23-p40, IL-12p40, IL-13, IL-13R alpha2, IL-13R1, IL-15, IL-16, IL-17, IL-17A, IL-17B, IL-17C, IL-17F, IL-17R, IL-18, IL-18BP alpha, IL-18R beta, IL-1a, IL-1B, IL-1R4/ST2, IL-1ra, IL-1RI, IL-1RII, IL-2, IL-21, IL-21R, IL-22 IL-23, IL-25, IL-28A, IL29, IL-2Ra IL-2Rbeta, IL-2Rgamma, IL-3, IL-31, IL-33, IL-4, IL-5, IL-5Ralpha, IL-6, IL-6R, IL-7, IL-8, IL-9, Insulin, IP-10, I-TAC, Latency Associated Peptide of TGF beta 1, Leptin, Leptin R, LIF Light, LIMPII, L-Selectin, Luteinizing hormone, LYVE-1, Marapsin, MCP-1 (MCAF), MCP-2, MCP-3, MCP-4, M-CSF, M-CSFR, MDC, MICA, MICB, Midkine, MI, MIG, MIP-1a, MUP-1b, MMP-1, MMP-10, MMP-13, MMP-2, MMP-3, MMP-7, MMP-8, MMP-9, MMP-9, MPIF-1, MSP-a, NCAM-1, NGFR, Nidogen-1, NrCAM, NRG1-beta1, NT-3, NT-4, Oncostatin M, Osteopontin, Osteoprotegerin, PAI-I, PDGF-AA, PDGF-AB, PDGF-bb, PDGFR beta, PDGFRalpha, PECAM-1, PLGF, Procalcitonin, Prolactin, PSA, PSA-free, PSA-total, RAGE, RANK, RANTES, Resistin, S-100b, SAP, sCD40L, SCFR, SCGF-b SCYB16, SDF-1a, SDF-1 beta, Serum Amyloid A, sgp130, ShhN, Siglec-5, Siglec-9, Soluble IL-2 Receptor α sIL-2Rα, Soluble IL-6 Receptor sIL-6R, Soluble TNF Receptor I sTNFRI, Soluble TNF Receptor II sTNFRII, sTNFRI, sTNFRII, TACE, Tau, TECK, TGF beta, TGF beta1, TGFalpha, TGFbeta2, TGFbeta3, Thrombopoietin, Thyroglobulin, Tie-1, Tie-2, TIM-1, TIMP-1, TIMP-2, TIMP-4, Tissue Plasminogen Activator, TNF receptors, TNF-α, TNF-b, TRAIL, TRAILR2, TRAILR3, TRAILR4, Trappin-2, TREM-1, Troponin-I, TSH, TSLP, Ubiquitin+1, uPAR, VCAM-1, VE-Cadherin, VEGF VEGF-A, VEGF-C, VEGF-D, VEGFR2, VEGFR3, XCL1/Lymphotactin, and XEDAR. The group from which biomarkers may be selected may further include C4a and C3a complement split products, e.g., Complement factors including but not limited to those of the Classical pathway, C1 complex, C1q, C1r, C1s, C4, C2; the Lectin pathway, MBL, MASP-1, MASP-2; the Alternative pathway; C3, Factor B, Factor D, Properdin 20; the Membrane attack complex, C5, C6, C7, C8, C9; Control proteins, C1 inhibitor, C4 binding protein, Factor I, Factor H; Receptor/membrane proteins, Decay-accelerating factor, Homologues restriction factor; and Anaphylatoxin receptors, C3a/C4a, C5a, C3 binding proteins, CR1, CR2, CR3, and CR4. The group from which biomarkers may be selected may further include Arachidonic acid, leukotrienes (A4, C4, D4 AND E4), prostaglandins (PGD2, PGE2, PDF2, PGH2, PGI2, PGF1Alpha, PGI2) and subtypes of thereof, and, LTB4.

Biomarkers and LD

The immune system produces biomarkers that can increase or decrease in response to an infection, for example, LD. For example, excess interferon gamma (INF-γ) has been found in early Lyme disease patients with an erythema migrans (EM) rash. However, other cytokines, e.g., interleukin-1 beta (IL-1β) and tumor necrosis factor—alpha (TNF-α) were found to be more prevalent in later, chronic LD infection. Although this distinguishes groups on a statistical basis, it is not sensitive or specific enough to differentiate, diagnose, or specify treatment of subjects. It has now been found that the identification of the presence of multiple biomarkers expressed in specific combination—a biomarker signature—may be utilized to differentiate LD from other diseases for the purpose of diagnosis and treatment. Further, biomarker signatures may define whether an infected subject, human or other species, has LD and requires treatment. The terms "subject" as used herein refers to a mammal including a non-primate (e.g., cow, pig, horse, dog, cat, rat, deer, and mouse) and a primate (e.g., monkey and human). Single host response markers are rarely sufficient for accurate diagnosis; rather, as disclosed herein, it is the mathematically defined relationship among them described by logic formula equation that is derived from logistic regression among the combination of two or more, preferably at least tour, and more preferably 10-12 of these markers that reveals the underlying network of LD host response that is critical for differentiation, diagnosis and treatment. The following biomarkers are examples of analytes that provide information about the immune network response: Eotaxin, IFN.gamma, SDF.1a.B, ENA.78, Fractalkine, IL.4, IL.1b, IL.6, CTACK, SAP, I.309, TICK, MCP.3, PDGF.B, IL.8, BCA.1, SCYB16, GCP.2, MCP.2, MCP.4, MIP.3b, TNF.a, Ferritin, Procalcitonin, 6Ckine, MIP.3a, MPIF.1, a.2.macroglobulin, MIG, TPA, TRAIL, B.NGF, IL.10, IL.2, MIP.1d, VEGF, MCP.1, IL.5, Gro.a, IL.16, IP.10, MDC, MIP.1a, MIP.1B, CRP, MIF, Eotaxin.2, Eotaxin.3, GM.CSF, Gro.B, I.TAC, and TARC.

This invention may include other markers that similarly provide information about the underlying immune network and is not restricted to the specific biomarker examples provided herein. The utility of the invention is founded in the biomarker signature comprising a salient combination. The methodology and assay resulting from the discovery of biomarker signatures may be used as the sole evaluation for a subject, or alternatively, may be used in combination with. other diagnostics and treatment methodologies.

Biomarker Assessment and Evaluation

For purposes of assessment and evaluation, choice of biomarkers was based on evidence of ability to differentiate LD infected subjects from subjects having other diseases with similar symptoms, e.g., bacterial, viral, and autoimmune, in a 1) t-test or 2) ROC curve or 3) known to be produced or related to early immune responses or 4) as a result of computer powered analysis of multiple possibilities, or a combination thereof. The receiver operating characteristic (ROC) curve or table is a statistical tool commonly used to evaluate the utility in clinical diagnosis of a proposed assay. The ROC addresses the sensitivity and the specificity of an assay. Therefore, sensitivity and specificity values for a given combination of biomarkers are an indication of the accuracy of the assay. The ROC curve is the most popular graphical tool for evaluating the diagnostic power of a clinical test. A number representing the fraction of the total graphical area under the curve (AUC) can be derived, is a widely used method of evaluating a potential diagnostic tool without the need of evaluating a graph. Sometimes the AUC of a subset of the space is used. This type of evaluation looks at the sensitivity at each specificity of the test. Similar information can be obtained by looking at a table of sensitivities at various specificities, and used to generate a ROC curve. Sensitivity relates to the ability of a test to correctly identify a condition, while specificity relates to the ability of a test to correctly exclude a condition. In addition, Leave-One-Out cross validation indicates the accuracy of a LOGIT derived analyte. The present invention has employed these types of analysis to evaluate and determine a unique biomarker signature of 30 biomatkers from which a combination of two or more biomarkers may be effectively used in the differentiation and diagnosis of LD.

In use, the present invention creates a new derived number, output value or score, which can be treated as a single "test" for ROC curve and AUC analysis. This approach allows use of these methods and comparison with other clinical assays that typically are the results of single analytes. The results from the statistical analysis performed provide an output value or score that can be directly translated into the probability that a sample comes from a subject with LD not a different disease. A score above a certain cutoff threshold, for example 50% is indicative of the presence of LD and a score below the cutoff threshold is indicative of the absence of LD. Nonetheless, the AUC can still serve as a general measure of the accuracy of the derived score or derived probability. These numbers derived, via the methods in the examples, provide excellent AUCs, while single biomarkers do not. Thus, scores indicative of presence or absence of the LD as opposed to another disease with similar symptoms are provided as is a method of differentiation and diagnosis that indicates appropriate treatment.

Via the techniques described herein, unique biomarker signatures have been discovered in LD providing a means of differentiation, diagnosis, and treatment. Differentiation and diagnosis are important because early and appropriate treatment have the greatest chance of a cure; delayed treatment is associated with the severe chronic form of the disease. LymeDisease.org published a Health Policy paper based on a survey of Lyme patients, many of whom might not have had such severe symptoms had they been diagnosed and treated promptly, which reported that in this group: 84% not diagnosed within 4 months of onset; 25% had been on disability; 50% see more than 7 physicians before diagnosis; 95% had LD for more than 2 years; 65% cut back on school or work; and, 25% were children.

Disclosed herein are particular biomarkers found to be associated with LD and which can be used in combination as a biomarker signature for differentiation and diagnosis of LD, and indicate subsequent treatment thereof. More specifically, disclosed herein are equations based on specific quantitative biomarker values found to be associated with LD immune phenotype, and thus LD. Such biomarker signatures may be useful for differentiation purposes, diagnostic purposes, treatment purposes, for methods for predicting treatment response, methods for monitoring disease progression, and methods for monitoring treatment progress, as described in further detail herein. Further applications of the LD biomarker signature include assays as well as kits for use with the methods described herein.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, a "sample," such as a biological sample, is a sample obtained from a subject. As used herein, biological samples include all clinical samples including, but not limited to, cells, tissues, and bodily fluids, such as: saliva, tears, breath, blood; derivatives and fractions of blood, such as filtrates, dried blood spots, serum, and plasma; extracted galls: biopsied or surgically removed tissue, including tissues that are, for example, unfixed, frozen, fixed in formalin and/or embedded in paraffin; tears; milk; skin scrapes; nails, skin, hair; surface washings; urine; sputum; bile; bronchoalveolar fluid; pleural fluid, peritoneal fluid; cerebrospinal fluid; prostate fluid; pus; or bone marrow. In a particular example, a sample includes blood obtained from a subject, such as whole blood or serum.

Methods for differentiating, diagnosing, predicting, assessing, and treating LD in a subject include detecting the presence or absence of one or more biomarker signatures described herein, in a subject's sample. The biomarker(s) may be isolated or, more typically quantified without isolation, from a biological sample using standard techniques. The sample may be isolated from the subject and then directly utilized in a method for determining the level of the biomarkers, or alternatively, the sample may be isolated and then stored (e.g., frozen) for a period of time before being subjected to analysis.

In some embodiments, the present invention is directed to a method of differentiating, diagnosing, and treating LD in a subject comprising the steps of:
  obtaining a sample from the subject;
  detecting in the sample the presence of a biomarker signature differentiating LD from other diseases; and
  administering a therapeutic treatment to the subject based on the biomarker signature detection results.

In some embodiments, predicting an increased likelihood of the subject having LD based on the presence or absence of a biomarker signature is further included.

In some embodiments, combinations of two, three, four, five, six, seven, eight, nine, ten, eleven, twelve, or more biomarkers may be detected in the sample from the subject.

In some embodiments, a method of differentiating, diagnosing, and treating LD in a subject comprising the steps of:
  obtaining a sample from the subject;
  detecting in the sample the expression levels of a combination of two or more analytes selected from the group consisting of Eotaxin, IFN.gamma, SDF.1a.B, ENA.78, Fractalkine, IL.4, IL.1b, IL6, CTACK, SAP, I.309, TECK, MICP.3, PDGF.B, 1L.8, BCA.1, SCYB16, GCP.2, MCP.2, MCP.4, MIP.3b, TNF.a, Ferritin, Procalcitonin, 6Ckine, MIP.3a, MPIF.1, a.2.macroglobulin, MIG, and TPA, wherein the detection of the presence or absence of the combination of biomarkers is indicative of LD infection; and
  administering a therapeutic treatment to the subject.

Another embodiment of the invention includes an assay and/or kit for differentiating and diagnosing a LD infection comprising reagents, probes, buffers; antibodies, or other agents that bind to biomarkers; signal generating reagents, including but not limited fluorescent, enzymatic, electrochemical; or separation enhancing methods, including but not limited to beads, electromagnetic particles, nanoparticles, binding reagents, for the detection of a combination of two or more biomarkers indicative thereof In some embodiments, the probe and the signal generating reagent may be one in the same. The agents that bind to biomarkers provided as part of an assay or kit further comprise agents that correlate directly to said biomarkers.

Techniques of use in all of these methods are discussed below. Numerous researchers have looked at biomarkers in a wide variety of disease, and specifically in LD. See, for example, Soloski et al. ((2014) PLoS ONE 9(4):e93243), hereby incorporated by reference in its entirety, including supplemental materials and deposited materials, as an example study of 65 cytokines. Soloski teaches that nearly half of the LD patients studied have patterns of cytokines that they call "low responders" that are similar to controls without disease. Despite sophisticated analysis using statistical methods and elegant "heat maps," the Soloski team found no biomarker patterns diagnostic of LD or capable of differentiation between LD and other like-symptom diseases. In contrast, the instant invention applies alternative mathematical and statistical approaches on carefully selected biomarker sets, discloses the unexpected results of exhibited biomarker patterns that reveal underlying immune networks, and provides equations that allow accurate differentiation of LD from other diseases.

Identification of Biomarker Signature(s):

For the variable and biomarker signature selection, LOGIT logistic regression (LR) models containing about 10 analytes were chosen in order to allow accurate separation and limit over-fitting. Three approaches were used to select the analytes included in the biomarker signatures. One method was to determine which analytes individually did the best job of distinguishing between Lyme and Not-Lyme cases, by means of parametric and non-parametric two-sample tests. Collections of analytes that showed statistically significant ability to separate Lyme from Not-Lyme cases were then used in LR models, as shown in Examples 1-5.

A secondary approach of performing single-variable logistic regression on all analytes yielded the same set of candidates, in the same rank order, as non-parametric two-sample tests. Therefore, no new candidate analytes resulted from this process.

In an attempt to find models that might outperform those chosen through systematic variable selection, the process of randomly selecting 10-analyte LR models was performed. Approximately 300,000 such models were examined. Since there are 52,179,482,355 possible ways of selecting a 10-analyte model from the 58 analytes that were measured, only a tiny fraction of all cases was sampled. Nonetheless this approach proved useful in uncovering several, well performing models.

The LR models were evaluated that resulted from the variable selection phase by considering the effectiveness of the model based on the area under the curve (AUC) of the receiver operating characteristics (ROC) curve that resulted from the model. Since an LR model with 10 independent variables may easily over-fit the data, resulting in an overly optimistic assessment of the model's effectiveness, the model selection process was further refined by considering only those models that showed little over-fitting as determined by industry standard cross-validation procedures.

Thus, the Leave One Out (LOO) cross validation method, unlike the 10× cross validation method, yielded a completely stable result each time it was run, and was therefore used to rank the excellence of the model.

Logistic Regression

The first approach was to perform logistic regression (LR) of Lyme disease status (Lyme or other disease) on selected sets ("models") of biomarkers (also referred to as independent variables, or IVs) to determine if the IVs adequately differentiated LD from other diseases. Logistic regression can be performed either using the original measured values of IVs, or each IV can be scaled (by subtracting its mean and then dividing by its standard deviation) prior to performing the regression. In either case, the result of LR is a linear function of the IVs, whose coefficients depend on Lyme disease status and the values of the IVs for each subject. This linear function predicts the (log) odds that a subject has Lyme disease. The predictive results are identical whether raw or scaled values are used, but the specific equations that result from the two approaches can be different. Logistic regression may optionally include additional variables, e.g., subject age, gender, BMI, genotype, and/or geographical region, as a number of these variables may alter the cytokine, chemokine and immune response.

Each model results in a different equation for differentiating Lyme disease status following the logistic regression process. Thus, multiple IVs are used in a model that has predictive value far in excess of individual analytes. It is only through the IV's, or biomarkers, inclusion in the equation that the role of that analyte to differentiate Lyme disease is useful.

Once LR has been performed, the results can be handled in several ways. To make actual predictions of Lyme disease status, a specific (log) odds threshold is chosen, and those subjects whose odds are higher than the threshold are differentiated as having Lyme disease as opposed to another disease, and the remainder declared not to have Lyme disease. Typically the probability threshold is between 30-60%. While most typically it is 50%, these examples found illustrate that 30% is better.

In order to evaluate the accuracy of the test, compared were the known condition of each subject with the predicted condition obtained, and the sensitivity and specificity of the LR of a chosen threshold. A second process is to plot sensitivity versus specificity for potential threshold value or selected values such as every 5%. The resulting plot (or table), referred to as a receiver operating characteristic (ROC) curve, provides a synoptic view of the effectiveness of the particular combination of IVs. One convenient way of summarizing the entire ROC curve is by taking the area under it (AUC). Another is to examine the area under the critical region reflecting the specificities above 80% (HS_ROC).

Several candidate models (sets of IVs) were selected based on different criteria, such as having t-test scores with p values below certain levels, and/or being involved in the early stages of immune response, and/or being easily measured clinically. For each such model LR was performed and plotted the resulting ROC curve, ROC table, AUC and HS-AUC were evaluated thereby providing a visual and or numerical means of comparing the benefits and/or accuracy of the different IV candidate sets.

Based on the size of the data set used in the analysis, the number of IVs in any candidate set was limited to approximately 10, in order to avoid overfitting of the LR results.

To check for overfitting, several cross validation tools were applied to each LR model. As another means of reducing overfitting several standard procedures for reducing the dimensionality of the LR model were examined.

Stepwise (logistic) regression reduces dimensionality by eliminating an IV from the model if its presence does not significantly improve the performance of the model. Principal components and partial least squares (logistic) regression, reduce dimensionality by means of procedures that take into account the manner in which the IVs correlate with one another (and with the response variable, in the case of partial least squares).

Assays, Kits, and Apparatuses:

An assay for analysis of subject samples for differentiating, diagnosing, and/or treating LD is provided. An assay may be provided individually or as part of a kit. Typically, an assay comprises at least one protein probe (detection agent) for a protein such as an antibody, aptamer or other protein binding compound or at least one pair of reagents, said probe or reagents including antibodies, aptamers, or other biomarker binding materials; and a substrate or homogenous reaction for the detection of an analyte. An assay for a biomarker signature may contain multiple probes corresponding to multiple analytes. The substrate may comprise, for example, beads, plates, glass slides, protein spots in microtiter wells, or other wells, or a microarray. The assay and/or kit may further comprise agents that generate detectable signals, where the agent may include, for example, light, enzyme reactions, electrochemical changes, fluorescent materials, plasmon resonance, magnetic signals, light, interference with light, or other signals known in the art. The probes may be bound to a substrate so that a change is immediately detectable by mass cantilevers, optical changes such as reflectance or interference, or other changes when the analyte is bound to the probe on the substrate. In some methods of quantifying analytes, a competitive assay may be employed. Assays and/or kits optionally include buffers, vials, microtiter plates or other solid substrates, and instructions for use. In some examples known in the art, assays and/or kits are intended to perform homogeneous assays, and thus, do not contain reagents or methods to physically separate the bound and unbound materials. Such assays and/or kits may use fluorescent energy transfer or micro environment transfer of substrates.

In the assay and/or kit aspect of the invention, provided is a substrate comprising detection agents specific for at least two biomarkers selected from Eotaxin, IFN.gamma, SDF.1a.B, ENA.78, Fractalkine, IL.4, IL.1b, IL.6, CTACK, SAP, I.309, TECK, MCP.3, PDGF.B, IL.8, BCA.1, SCYB16, GCP.2, MCP.2, MCP.4, MIP.3b, TNF.a, Ferritin, Procalcitonin, 6Ckine, MIP.3a, MP1F.1, a.2.macroglobulin, MIG, and. TPA for use in a method for differentiating and diagnosing LD in a subject according to the present invention. Preferably, the substrate has at least two probes immobilized thereon, more preferably three, four, or more probes, wherein each probe is specific to an individual biomarker comprising the biomarker signature. As used herein, the term "specific" means that the probe binds only to one of the biomarkers of the invention with relatively little other binding. in some embodiments, higher specificity of the probe reactions is obtained by using probe pairs and recording a positive signal only if both bind as is typical in a "sandwich assay." Kits of the present invention may further comprise additional reagents, substrate/reaction surfaces, and/or instructions for use.

Preparation of Sample(s) for Analysis

Samples may be prepared for analysis using any technique known to those skilled in the art for determining the presence of biomarkers While cell extracts can be prepared using standard techniques in the art, the methods generally use serum, blood filtrates, blood spots, plasma, saliva, tears, or urine prepared with simple methods such as centrifugation and filtration. The use of specialized blood collection tubes such as rapid serum tubes containing a clotting enhancer to speed the collection of serum and agents to prevent alteration of the biomarkers is one method of preparation. Another method utilizes tubes containing factors to limit platelet activation, one such tube contains citrate as the anticoagulant and a mixture of theophylline, adenosine, and dipyrimadole.

The preferred methodology is based on the overall concept of immune-detection. Such detection may be performed in a laboratory, point of care, clinical, or other setting, and may be incorporated into transportable or hand-held devices. A quantitative immunoassay, e.g., ELISA or its equivalent, may be used to detect the amount of protein. A multi-analyte method of analysis enabling several proteins to be detected and quantified simultaneously may be used.

Blood and urine samples were collected from subjects in three disease groups entitled: Lyme-Like, Acute Lyme, and Chronic Lyme. The Lyme-Like subject criteria for selection included one or more of the following symptoms: fever, sore throat, headache, fatigue, body aches, inflammation, stomach ache, joint pain, or observations (tick bite) consistent with LD. The Acute Lyme disease group was defined as previously diagnosed with LD via bulls eye rash or the CDC two-tier test system within the first 8-weeks after a tick bite. The Chronic Lyme disease subjects were identified as 1) previously diagnosed with LD via bulls eye rash or the CDC two-tier test system, and 2) previously treated but still exhibiting symptoms, such as, fever, sore throat, headache, fatigue, body aches, inflammation, stomach ache, and/or joint pain.

A total of 100 serum samples from 2 sites were used. All serum was collected in standard clotting tubes(("red tops") or "Serum Separator Tubes (SST)" from Becton Dickenson, samples were allowed to clot for 30 min and then processed promptly, 59 were collected from the Northern Virginia site (Nova Medical and Urgent Care Center, Inc.) and 41 from a site on Martha's Vineyard (Vineyard Medical Care, LLC), A total of 77 presented with symptoms that can occur in patients with Lyme disease. These patients had problems including various bacterial (sinusitis, Strep, skin infections), viral, or other symptomatic illness involving the immune system. The Vineyard samples included 23 normal cases with no symptoms.

They also included 18 Lyme cases who were negative at the time of collection but who subsequently seroconverted, Thus, these are documented as very early stage positive serum. Among the NoVa population, there were 50 negative for Lyme but with symptoms determined to be due to other conditions, 8 diagnosed with Lyme as indicated by the presence of EM but with no positive blood test, and 1 case with a positive test for Lyme (2-tier). The 77 samples were analyzed separately in some cases, omitting the 23 normal (no symptoms) samples. Overall, there were 56 females and 44 males, with an average age of 40.6 (sd=15.4; median 39) and a range of 16 to 73.

Specifically, blood samples were drawn from each subject into 2-10 ml serum separator tubes (SST) and 4-5 ml rapid serum tubes (RST). After the last sample was collected, the RST tubes were spun down for 5 minutes according to the instructions found at www.bd.com/bacutainer/pdfs/VS8876.pdf. Immediately after centrifugation, the 4 RST were decanted and aliquotted into cryovials, each containing 1 ml. The SST samples were allowed to clot for 35 minutes±5 minutes bethre centrifugation was performed according to the instructions found at www.bd.com/vacutainer/pdfs/techtalk/techtalk_november2005_vs7436.pdf. Processed samples were frozen immediately thereafter and stored on their side or upside down in a closed container outfitted to prevent melting during freezer defrost cycles. Subjects also provided urine samples that were centrifuges, aliquotted into 5 ml samples, and frozen. All samples were stored at −20° C. prior to shipment on dry ice to biomarker detection and analysis site.

Biomarker Detection

Methods for detecting biomarkers, e.g., cytokines, chemokines and prostaglandins in samples are well known in the art. In one example, detection includes detecting expression of a biomarker signature, wherein said signature is comprised of a combination of at least two or more biomarkers. Detection can include classic sandwich or competitive immunoassays, these may be done in ELISA format or any of numerous commercial and available research methods known in the art, including but not limited to: Randox, Luminex, Quanterix, Cyplex, MagArray, plasmon resonance methods, and any method that detects the presence of a biomarker by the binding of a antibody, aptamer, or other binding molecule. Chemokines and Cytokines, as enumerated in the Examples, were analyzed using Luminex bead systems supplied by Bio-Rad Laboratories (Hercules, Calif.) according to the manufacturer's instructions.

Analysis

For use of the two or more biomarkers in the diagnostic method of the present invention, a suitable mathematical method, e.g., logistic regression, is used. Logistic regression is run on the chosen biomarker values on the subjects. An ROC curve may be used to assess the relationship between sensitivity and specificity. Leave One Out Cross Validation Accuracy (LOO) may be used to assess the overall accuracy of the derived model.

Other embodiments in accordance with the principles of the present invention include, for example, a system for determining whether a subject possesses a biomarker signature and/or score indicative of a differential diagnosis of LD. For example, the system may include an on-site storage device or central server configured to store data produced from the sample suspected of LD infection, as well as evaluation algorithms for determination of score and subsequent treatment. Such systems may not include the algorithm, and may further include a processor that communicates with the storage device or server, wherein the processor and/or server executes software to obtain and/or scale data produced from the sample, process the data, and determine a score indicative of LD status. In some embodiments, both systems containing computation ability and communication ability with a server in real or delay time may occur.

The present invention is further illustrated by the following examples that should not be construed as limiting. The contents of all references, patents, and published patent applications cited throughout this application, as well as any Figures, are incorporated herein by reference in their entirety for all purposes.

Provided is a method for differentiating, diagnosing, and treating a subject suspected of having LD, comprising determining the expression of at least two biomarkers in a sample, and mathematically establishing the significance of the concentration of the biomarkers, wherein the at least two biomarkers are selected from the group consisting of Eotaxin, IFN.gamma, SDF.1a.B, ENA,78, Fractalkine, IL.4, IL.1b, IL.6, CTACK, SAP, I.309, TECK, MCP.3, PDGF.B, IL.8, BCA.1, SCY.B16, GCP.2, MICP.2, MCP.4, MIP.3b, TNF.a, Ferritin, Procalcitonin, 6Ckine, MIP.3a, MPIF.1, a.2.macroglobulin, MIG, and TPA.

In a preferred embodiment, the at least two biomarkers are selected from the group consisting of Eotaxin, IFN.gamma, SDF.1a.B, ENA.78, Fractalkine, IL.4, IL.1b, IL.6, CTACK, SAP, I.309, TECK, and MCP.3. In another preferred embodiment, the at least two biomarkers are selected from the group consisting of PDGF.B, IL.8, SCYB16, GCP.2, MCP.2, MCP.4, MIP.3b, TNF.a, Ferritin, Procalcitonin, 6Ckine, MIP.3a, MPIF.1, a.2.macroglobulin, MIG, and TPA. In some embodiments, the at least two biomarkers further comprise at least one biomarker selected from the group consisting of TRAIL, B.NGF, IL.10, IL.2, MIP.1d, VEGF, MCP.1, Gro.a., IL.16, IP.10, MDC, MIP.1a, MIP.1B, CRP, MIF, Eotaxin.2, Eotaxin.3, GM.CSF, Gro,B, I.TAC, and TARC. Combinations of three or more biomarkers may also be preferred as they evidence some of the highest sensitivity and specificity.

Biomarker concentrations can be determined by contacting the sample with a substrate having probes specific for each of the biomarkers included in the biomarker signature. Biomarker and respective probe interactions may be monitored and quantified using various techniques that are well-known in the art. For biomarker signature quantification, a solid substrate device may be preferred, many of which are known in the art.

Data corresponding to a specific set of biomarkers, a model, was analyzed with mathematical models and algorithms disclosed herein, thereby generating a sensitive and specific assay for differentiation and diagnosis of Lyme disease. All of the data were analyzed by using logistical regression, and/or Support Vector Machines (SVM). ROC analysis was used to estimate the sensitivity/specificity relationship for each analysis performed, the results of which are summarized herein and set forth in detail in Table X. In order to evaluate the robustness of the methods, the available data sets were randomly divided into training and validation sets 1000 times. The AUCs for each using various methods is presented. Thus, although SVM produced the highest AUC on training data, regression methods were the most robust in use, proving the equations, especially the one generated by logistic regression, are not simply a fit for the training data but a useful method to parse the validation/testing set, and thus, validated as clinically relevant.

Additional methods of statistical analysis known in the art, including principal components analysis (PCA), principal coordinates analysis, principal coordinates regression, partial least squares, independent coordinates analysis, forward stepwise regression, random forest analysis, and/or cluster analysis may also be used to analyze data, either alone or in combination for purposes set forth herein.

The performance of each non-obvious equation in the examples below was evaluated by area under the receiver operating characteristic curves (AUC) which ranged from a random 0.5 to 0.99. Some biomarkers negatively correlated with LD. Examples of biomarker signatures evaluated as described herein are set forth in Examples 1-5. These are non-limiting examples of panels that measure the biomarker signature(s) capable of differentiating LD from other like-symptom diseases. These results identify an immune network and anomalies unique to Lyme disease. Several illustrations of models (sets of biomarkers) detecting anomaly in the network are provided hereinbelow. Several biomarker signatures, each identifying the immune network associated with LD can be used to differentiate and diagnose LD, Example 1

Stepwise Regression of Analytes with Good p Values

A BioRad 40 Plex consisting of the following was run on a 1:4 dilution of serum: 6Ckine, MIG, GCP-2, IL-6, I-309, IFN-gamma, SDF-1a+B, I-TAC, MCP-3, IL-16, MCP-4, MDC, Eotaxin-2, GM-CSF, MIF, TNF-a, MPIF-1, IL-2, IL-1b, Eotaxin, TECK, IP-10, IL-4, MCP-1, IL-8, MIP-1a, IL-10, MCP-2, Gro-a, MIP-3a SCYB16, Eotaxin-3, MIP-1d (CCL15), TARC, CTACK, ENA-78, BCA-1, MIP-3b, Fractalkine, Gro-B was run using the manufacturers reagents and instructions. In addition a 5-plex was run on serum using a 1:100 serum dilution; this contained: Ferritin, Fibrinogen, Procalcitonin, Serum Amyloid A, Tissue Plasminogen Activator. Further a 4 Plex diluted 1:10,0000 containing the following analytes was also run: a-2-macroglobulin, CRP, Haptoglobin, SAP. The results of these assays were used in each of the examples.

Analytes were chosen from those that had the lowest p-values on t-tests for Lyme versus not-Lyme. LOGIT regression was then run using these analytes. With a large number of analytes in the model (Line A table 1), overfitting, as indicated by low LOO cross-validation accuracy was seen. "Stepwise Regression", a standard statistical method for reducing the number of variables in a regression model, generated improvement as seen on line B. To further improve the results, two analytes found to be important by the computer search method illustrated below were added, and then using stepwise reduction (lines C) generated better performance. Table 1 shows several examples of performance based on this set of analytes; key measures are in bold

TABLE 1

Performance of analytes with good p-values

| | | # Analytes | AUC | xval LOO | \multicolumn{5}{c}{Sensitivity (in italics) at the specificity indicated in the column header} |
|---|---|---|---|---|---|---|---|---|---|
| | | | | | 1 | 0.95 | 0.9 | 0.85 | 0.8 |
| A | Good p-values analytes (all) | 18 | 0.928 | 0.66 | *0.59* | *0.67* | *0.78* | *0.81* | *0.81* |
| B | Stepwise reduced analytes | 5 | 0.924 | 0.78 | *0.56* | *0.59* | *0.70* | *0.77* | *0.89* |
| C | Further stepwise reduction; CTACK & TECK added | 7 | 0.970 | 0.86 | *0.70* | *0.89* | *0.93* | *0.93* | *0.93* |

A) MCP.3, SDF.1a.B, CRP, IP.10, IL.6, B.NGF, IL.IB, a.2.macroglobulin, SAP, GCP.2, Gro.B, Procalcitonin, TARC, MCP.4, IL.2, IL.4, IL.10, Eotaxin.3
B) MCP.3, SDF.1a.B, a.2.macroglobulin, SAP, Gro.B, IL.2
C) MCP.3, SDF.1a.B, a.2.macroglobulin, SAP, Gro.B, CTACK, TECK

Example 2

Models Comprising 10 Biomarker Analytes

In order to discover better models brute force (the use of computer power to examine large numbers of combinations) computing power was used to examine large numbers of potential combinations of 10 analytes. Table 2 shows performance of a number of examples of excellent performance obtained by this methods. Again, excellent performance as shown by LOO validation of above 0.9 as well as high AUC and high sensitivity (about 90%) at a specificity of 95% is seen.

TABLE 2

Good LOO performance

| | | | Sensitivity (in italics) at the specificity indicated in the column leader | | | | |
|---|---|---|---|---|---|---|---|
| # Analytes | AUC | LOO | 1 | 0.95 | 0.9 | 0.85 | 0.8 |
| A | 10 | 0.954 | 0.91 | *0.89* | *0.89* | *0.89* | *0.93* | *0.93* |
| B | 10 | 0.959 | 0.91 | *0.52* | *0.93* | *0.93* | *0.93* | *0.93* |
| C | 10 | 0.950 | 0.91 | *0.78* | *0.89* | *0.89* | *0.89* | *0.89* |
| D | 10 | 0.944 | 0.91 | *0.63* | *0.89* | *0.93* | *0.93* | *0.93* |
| E | 4 | 0.943 | 0.91 | *0.52* | *0.93* | *0.93* | *0.93* | *0.93* |

A) MCP.3, Gro.B, MIP.1a, 6Ckine, MCP.2, IL.1b, IL.6, Procalcitonin, Eotaxin.3, TECK
B) IL.4, IFN.gamma, Fractalkine, GM.CSF, I.309, TNF.a, IP.10, SAP, ENA.78, MCP.3
C) TECK, GCP.2, SAP, TPA, MIG, MIP.3a, SCYB16, CTACK, MCP.3, MCP.2
D) IL.16, CRP, TPA, MIG, Eotaxin.3, IFN.gamma, I.309, MCP.3, Procalcitonin, MCP.4
E) MCP.3, I.309, SAP, TECK In total over 35 models (sets of analytes and specific equations) were identified that produced robust models with little overfilling as measured by LOO cross-validation accuracy of 0.91 or above and excellent AUCs (0.94 or higher). The combination of 30 markers was identified as the signature (sets A and B below) indicative of and capable of differentiating LD from other diseases with similar symptoms.

Of this 30 a subset group of 13 biomarkers, defined as (Set A) were used most often and a group of 17 biomarkers (Set B) were very used frequently, but not as often. Set A and Set B together make the core analyte pool of good models, biomarkers signature. The use of 2 or more is required, but not sufficient, to produce good models. Good models often used a combination of Set A or B biomarkers. Typically 50% of more of the markers were from Set A or B. In addition models typically used a small number, 1-4, analytes not included in Set A or B. The ones typically used are described in Table C (Set C)

Set A: Eotaxin, IFN.gamma, SDF.1a.B, ENA.78, Fractalkine, IL.4. IL.1b, IL.6, CTACK, SAP, I.309, TECK, and MCP.3

SET B: PDGF.B, IL.8, BCA.1, SCYB16, GCP.2, MCP.2, MCP.4, MIP.3b, TNF.a, Ferritin, Procalcitonin, 6Ckine, MIP.3a, MPIF.1, a.2.macroglobulin, MIG, and TPA SET C: TRAIL, B.NGF, IL.10, IL.2, MIP.1d, VEGF. MCP.1, IL.5, Gro.a, IL.16, IP.10, MDC, MIP.1a, MIP.1B, CRP, MIF, Eotaxin.2, Eotaxin.3, CM.CSF, Gro.B, I.TAC, and TARC Tables A, B, and C. Biomarker Signature Combinations.

Tables A, B and C show sets of analytes as rows. Table A contains set A analytes only. Each column is a different model that has a LOO of 0.91 or better. Table A continues on a separate page; the first page shows models a-q; the second page models r-kk. The analytes used are shown by asterisks; a typical model uses analytes from Set A, B and/or C. Model "a" on Table B is a continuation of model "a" on Table A. Thus the composition of each of the models a-kk can be read by reading down the column heading for that model through all 3 tables. Table B shows analytes in Set B. Table C shows analytes in Set C. Table D shows the performance characteristics of each model, and uses the same letters to identify a model as used in Tables A,B and C.

TABLE A

Set A, Models a-q

| | a | b | c | d | e | f | g | h | i | j | k | l | m | n | o | p | q |
|---|---|---|---|---|---|---|---|---|---|---|---|---|---|---|---|---|---|
| Eotaxin | * | | * | | | | | | * | | | | | | | | |
| IFN.gamma | | | | | | | | * | | | | | | | * | * | |
| SDF.1a.B | | | | * | | | * | | | | | | | | | | |
| ENA.78 | | | | | | | | | | * | * | | | * | * | | |
| Fractalkine | | | | | | | * | | * | | | | | | | * | * |
| IL.4 | | | | | | | | | | | | | | | | | * |
| IL.1b | | | | | | * | | | * | * | * | * | | | | | |
| IL.6 | | | | | | * | | * | | | | * | * | | | | |
| CTACK | | | | * | | | * | * | | | | * | | * | | | |
| SAP | * | | * | | | * | | | | | | | | | * | * | * |
| I.309 | * | | | | | | | * | * | * | | | | | | * | * |
| TECK | * | * | * | * | * | * | * | * | * | * | * | * | * | * | * | * | * |
| MCP.3 | * | * | * | * | * | * | * | * | * | * | * | * | * | * | * | * | * |

TABLE B

Set B, Models a-q

| | a | b | c | d | e | f | g | h | i | j | k | l | m | n | o | p | q |
|---|---|---|---|---|---|---|---|---|---|---|---|---|---|---|---|---|---|
| PDGF.BB | | | | | | | * | | | | | | | | | | |
| IL.8 | | | | | * | | | * | * | | | | | | | | |
| BCA.1 | | | | | | | * | | | | | | | | | | |
| SCYB16 | | | | | | | * | | | | | | * | | | | |
| GCP.2 | | | | | | | | | * | | | | * | | | | |
| MCP.2 | | | | | | | | | | | * | * | | | | | |
| MCP.4 | | | | | | | | | | | | * | * | | | | |
| MIP.3b | | | | | | | | * | | | | | | | | | |
| TNF.a | | | | | | | | | | | | * | | * | * | | |
| Ferritin | | | | | | | | * | | | | | | | | | |
| Procalcitonin | | | | | | | | | | | * | * | | | | | |
| 6Ckine | | | * | | | | | | | | | | | * | * | | |
| MIP.3a | | | | | * | | | | | | | | * | | | | |
| MPIF.1 | | | | | | | | | * | * | | | | | | | |
| a.2.macroglobulin | | | | | | | | | | | | | | | | | * |
| MIG | | | | | | | | | | | | | | | | | |
| TPA | | | | | | | | | * | | | | | | * | | |

TABLE C

Set C Models a-q

| | a | b | c | d | E | f | g | h | i | j | k | l | M | n | o | p | q |
|---|---|---|---|---|---|---|---|---|---|---|---|---|---|---|---|---|---|
| TRAIL | | | | | | | | | | | | | * | | | | |
| B.NGF | | | | | | | | | | | | | | | | | |
| IL.10 | | | | | | | | | | | | | * | | | | |
| IL.2 | | | | | | | | | | | | | | | | | |
| MIP.1d | | | | | | | | | | | | | | | | | |
| VEGF | | | | | | | | | | | | | * | | | | |
| IL.5 | | | | | | | | | | | | | | | | | |
| Gro.a | | | | | | | | | | | | | | | | | |
| IL.16 | | | | | | | | | | | | | | | | | |
| IP.10 | | | | | | | | | | | | | * | * | | | |
| MDC | | | | | * | | | | | | | | | | | | |
| MIP.1a | | | | | | | | | | | * | | | | | | |
| MIP.1B | | | | | | | | | | | | * | | | | | |
| CRP | | | * | | | | | | | | | | | | | | |
| MIF | | | * | | | | | | | | | | | | | | * |
| Eotaxin.2 | | | | | | | | | | | | | | | | | |
| Eotaxin.3 | | | | | | | | | | | * | | | | | | |

Performance Statistics, Models a-q

TABLE C-continued

Set C Models a-q

|  | a | b | c | d | E | f | g | h | i | j | k | l | M | n | o | p | q |
|---|---|---|---|---|---|---|---|---|---|---|---|---|---|---|---|---|---|
| GM.CSF |  |  |  |  |  |  |  |  |  |  |  |  | * |  |  |  |  |
| Gro.B |  |  |  |  |  |  |  | * |  |  |  |  |  |  |  |  |  |
| I.TAC |  |  |  |  |  |  |  |  |  | * |  |  |  |  |  |  |  |
| MCP.1 |  |  |  |  |  |  |  | * |  |  |  |  |  |  |  |  |  |
| TARC |  |  |  |  |  |  |  |  |  |  |  |  |  |  |  |  |  |

|  | a | b | c | d | e | f | g | h | i | j | k | l | m | n | o | p | q |
|---|---|---|---|---|---|---|---|---|---|---|---|---|---|---|---|---|---|
| AUC | 0.97 | 0.94 | 0.94 | 0.95 | 0.96 | 0.97 | 1 | 0.97 | 0.97 | 0.97 | 0.94 | 0.94 | 0.95 | 0.96 | 0.96 | 0.96 | 0.97 |
| Xval LOO | 0.91 | 0.91 | 0.92 | 0.91 | 0.91 | 0.92 | 0.9 | 0.91 | 0.91 | 0.92 | 0.91 | 0.92 | 0.91 | 0.92 | 0.91 | 0.91 | 0.91 |

Set A, Continued, Models r-kk

|  | r | s | t | U | x | y | z | aa | bb | cc | dd | Ee | ff | gg | hh | ii | jj | kk |
|---|---|---|---|---|---|---|---|---|---|---|---|---|---|---|---|---|---|---|
| Eotaxin |  |  |  | * |  | * |  |  |  |  |  |  |  |  | * |  |  |  |
| IFN.gamma | * |  |  |  | * |  |  |  |  |  |  |  |  |  |  | * |  |  |
| SDF.1a.B | * |  | * | * |  |  |  |  |  |  |  |  |  | * | * |  |  |  |
| ENA.78 |  |  | * | * |  |  |  |  |  |  |  |  |  |  |  | * | * |  |
| Fractalkine |  |  |  |  |  | * |  |  |  | * |  |  |  |  |  | * | * |  |
| IL.4 | * |  | * | * | * |  | * |  |  | * |  |  | * |  |  | * | * |  |
| IL.1b |  | * |  |  |  |  |  |  | * |  | * |  |  | * | * |  |  |  |
| IL.6 |  | * |  |  |  |  |  | * |  | * | * | * |  |  | * |  | * |  |
| CTACK | * | * |  | * | * | * |  | * | * |  | * |  |  |  |  | * | * |  |
| SAP |  | * | * |  | * | * |  | * |  | * |  | * |  |  |  | * | * |  |
| I.309 | * | * |  |  | * | * | * | * |  | * |  |  |  | * |  | * | * |  |
| TECK | * | * | * |  | * | * | * | * | * | * | * | * |  |  | * | * | * |  |
| MCP.3 | * | * | * |  | * | * | * | * | * | * |  | * | * | * | * | * | * |  |

Set B, Continued, Models r-kk

|  | r | s | t | U | x | y | z | aa | bb | cc | dd | Ee | ff | gg | hh | ii | jj | kk |
|---|---|---|---|---|---|---|---|---|---|---|---|---|---|---|---|---|---|---|
| PDGF.BB |  |  |  |  |  |  |  | * |  |  |  |  |  | * |  |  |  |  |
| IL.8 |  |  |  | * |  |  |  |  |  |  |  |  |  |  |  |  |  |  |
| BCA.1 | * |  |  |  |  |  |  |  | * |  |  |  |  |  |  |  |  |  |
| SCYB16 |  | * |  |  |  |  |  |  |  | * |  |  |  |  |  |  |  |  |
| GCP.2 |  | * |  | * |  |  |  |  |  |  |  |  |  |  |  |  |  |  |
| MCP.2 |  | * |  |  | * |  |  |  |  |  |  |  |  |  |  |  |  |  |
| MCP.4 |  |  | * |  |  | * |  |  |  |  |  |  |  |  |  |  |  |  |
| MIP.3b |  |  |  | * | * |  |  | * |  |  |  |  |  |  |  |  |  |  |
| TNF.a |  |  |  |  |  |  | * |  |  |  |  |  |  |  |  |  |  |  |
| Ferritin |  |  |  |  |  |  |  |  |  | * | * |  | * |  |  |  |  |  |
| Procalcitonin |  |  |  |  | * |  |  |  |  |  | * |  |  |  |  |  |  |  |
| 6Ckine |  |  |  |  |  |  |  |  |  |  |  |  |  | * | * |  |  |  |
| MIP.3a |  | * | * |  |  |  |  | * |  |  |  |  |  |  |  |  |  |  |
| MPIF.1 | * |  | * |  |  |  |  |  |  |  |  |  |  |  | * |  |  |  |
| a.2.macroglobulin | * |  | * |  |  |  |  |  |  |  |  |  |  | * | * |  |  |  |
| MIG |  | * |  |  | * | * |  |  |  |  |  |  |  | * | * |  |  |  |
| TPA |  | * |  |  | * |  |  | * |  |  |  |  |  |  |  |  |  |  |

Set C Continued, Models r-kk

|  | r | s | t | u | X | y | z | aa | bb | cc | dd | ee | ff | gg | hh | ii | jj | kk |
|---|---|---|---|---|---|---|---|---|---|---|---|---|---|---|---|---|---|---|
| TRAIL |  |  |  |  |  |  |  |  |  |  |  |  |  |  |  |  |  |  |
| B.NGF | * |  |  |  |  |  |  |  |  |  |  |  |  |  |  |  |  |  |
| IL.10 |  |  |  |  |  |  |  |  |  |  |  |  |  |  |  |  |  |  |
| IL.2 |  |  |  |  |  |  |  | * |  |  |  |  |  |  |  |  |  |  |
| MIP.1d |  |  |  |  |  |  |  |  |  | * |  |  |  |  |  |  |  |  |
| VEGF |  |  | * |  |  |  |  |  |  |  |  |  |  |  |  |  |  |  |
| E_IL.5 | * |  |  |  |  |  |  |  |  |  |  |  |  | * |  |  |  |  |
| Gro.a |  |  |  |  |  | * |  | * |  |  |  |  |  |  |  |  |  |  |

-continued

| | r | s | t | u | X | y | z | aa | bb | cc | dd | ee | ff | gg | hh | ii | jj | kk |
|---|---|---|---|---|---|---|---|---|---|---|---|---|---|---|---|---|---|---|
| IL.16 | | | | | * | | | | | | | | * | | | | | |
| IP.10 | | | | * | | | | | | | | | | | | | | |
| MDC | | * | | | | | | | | | | | | | | | | |
| MIP.1a | | | | | | | * | | | | | | | | | | | |
| E_MIP.1B | | | | * | | | | | | * | | | | | | | | |
| CRP | | | | | * | | | | | | | | | | | | | |
| MIF | | | * | | | | | | | | | | | | | | | |
| Eotaxin.2 | | * | | * | | | | | * | | | | | | | | | |
| Eotaxin.3 | | * | | | * | | | | | | | | | | | | | |
| GM.CSF | | | | | | | | * | | | | | * | | | | | |
| Gro.B | | | | | | | | * | | | | | | * | | | | |
| I.TAC | | | | * | * | | | | | | | | | | | | | |
| MCP.1 | * | | | | | | * | | | | | | * | * | | | | |
| TARC | | | | | | | | | * | * | * | | | | | | | |

Performance Statistics, Continued, Models r-kk

| | r | s | t | U | x | y | z | aa | bb | cc | dd | Ee | ff | gg | hh | ii | jj | kk |
|---|---|---|---|---|---|---|---|---|---|---|---|---|---|---|---|---|---|---|
| AUC | 0.98 | 0.98 | 0.95 | 0.94 | 0.96 | 0.95 | 0.97 | 0.94 | 0.96 | 0.97 | 0.95 | 0.99 | 0.99 | 0.99 | 0.98 | 0.98 | 0.98 | 0.98 |
| Xval LOO | 0.92 | 0.91 | 0.91 | 0.91 | 0.91 | 0.91 | 0.91 | 0.91 | 0.91 | 0.91 | 0.91 | 0.9 | 0.87 | 0.87 | 0.88 | 0.87 | 0.87 | 0.91 |

Example 3

Model Comprising Set A Biomarker Analytes

It could be hypothesized that a model consisting only of analytes in Set A may be optimum. However, it was discovered, as described above, models containing at least one variable outside this group is as good or better. A model consisting entirely of markers in Set A and containing 10 analytes (MCP.3, TECK, I.309, SAP, IL.4, IL.6, IL.1b, Fractalkine, ENA.78, IFN.gamma) was made. The AUC of this equation was 0.98 and LOO and 10× cross validation showed values above 0.87 indicating robustness but potentially some overfitting (Below Table 3)

TABLE 3

| | | | | Sensitivity (in italics) at the specificity indicated in the column header | | | | |
|---|---|---|---|---|---|---|---|---|
| # Analytes * | AUC | xval LOO | Training accuracy | 1 | 0.95 | 0.9 | 0.85 | 0.8 |
| 10 | 0.980 | 0.87 | 0.95 | 0.93 | 0.93 | 0.93 | 0.93 | 0.93 |
| 8 | 0.979 | 0.91 | 0.94 | 0.89 | 0.93 | 0.93 | 0.93 | 0.93 |

In order to reduce potential overfitting and improve the LOO stepwise reduction was used. The results shown above indicate that reduction to 8 analytes improves LOO and reduces overfitting. This equation differentiates LD from other diseases in a subject where Logit sum of coefficients and Logit=log(Probablility/(1=Probablility)) derived from logistic regression multiplied by [analyte concentrations] is calculated as follows:

10 analyte equation:

$$\text{Logit} = 3.9 - 0.368*MCP.3 + 0.014*TECK + 0.322*I.309 - 0.0005*SAP - 0.426*IL.4 - 0.279*IL.6 + 0.117*IL.1b + 0.011*\text{Fractalkine} + 0.0035*ENA.78 - 0.037*IFN.\text{gamma}$$

8 analyte equation:

$$\text{Logit} = 4.3 - 0.366*MCP.3 + 0.016*TECK + 0.345*I.309 - 0.0006*SAP - 0.477*IL.4 - 0.259*IL.6 + 0.013*\text{Fractalkine} + 0.004*ENA.78$$

The 8 analyte model is a preferred embodiment. Based on an outcome of carrying out the method of the invention wherein the score is indicative of differentiating LD from other diseases or no disease, then the subject may be treated accordingly Key to the present invention is the power of biomarker signatures to differentiate and diagnose LD through high specificity and sensitivity. This aspect of the invention facilitates clinical diagnosis and informs subsequent treatment decisions.

Example 4

Model Comprising Set A and Set B

A model using the combination of IL.8, MCP.3, TECK, IL.6, Procalcitonin, MIP.3b, CTACK, GCP.2, SDF.1a.B, I.309 is illustrated below. This yielded improved performance compared to the above; AUC=0.973, Leave One Out Cross Validation Accuracy (LOO) of 0.92, Training accuracy of 0.96, and at a sensitivity of 0.96 at a specificity of 0.95. It is a preferred example; see line J in below table. This the most preferred embodiment.

The equation for this model is:

$$\text{Logit} = 5.94 - 0.053*IL.8 - 0.324*MCP.3 + 0.023*TECK - 0.145*IL.6 - 0.0002*\text{Procalcitonin} + 0.003*MIP.3b + 0.004*CTACK - 0.023*GCP.2 + 0.002*SDF.1a.B + 0.172*I.309$$

Example 5

Model Comprising_Set A, B and One from C
(Column 1)

TABLE 4

| | # Analytes | AUC | xval LOO | Training accuracy | \multicolumn{5}{c}{Sensitivity (in italics) at the specificity indicated in the column header} |
|---|---|---|---|---|---|---|---|---|---|
| | | | | | 1 | 0.95 | 0.9 | 0.85 | 0.8 |
| Example I | 10 | 0.967 | 0.91 | 0.94 | *0.85* | *0.89* | *0.89* | *0.89* | *0.93* |
| Example J | 10 | 0.973 | 0.92 | 0.96 | *0.56* | *0.96* | *0.96* | *0.96* | *0.96* |

I) IFN.gamma, Ferritin, I.309, Fractalkine, MCP.1, CTACK, TPA, TECK, MPIF.1, MCP.3
J) IL.8, MCP.3, TECK, IL.6, Procalcitonin, MIP.3b, CTACK, GCP.2, SDF.1a.B, I.309
I) Logit = −0.322 + 1.33*IFN.gamma + 0.00005*Ferritin + 0.14*I.309 − 0.003*Fractalkine + 0.031*MCP.1 + 0.005*CTACK − 0.002*TPA + 0.017*TECK − 0.01*MPIF.1 − 0.37*MCP.3

When a patient sample is diagnosed, the amount of each analyte is measured and the results inserted in the model equation. A probability of Lyme is thus determined. The likelihood of LD is thus calculated and the physician and patient can determine if treatment is appropriate.

Although the examples of the principles of the present invention have been described with respect to LD and treatment known to be effective therefor, now or in the future, it should be understood that the principles may be applied to other disease and/or infections exhibiting similar symptoms and/or signatures for diagnosis, differential diagnosis, and/or treatment.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features set forth herein.

What is claimed is:

1. A method comprising: a) obtaining a sample from a subject suspected of having Lyme disease; and b) detecting a biomarker signature in said sample, said biomarker signature comprising Monocyte Chemoattractant Protein 3 (MCP.3), Thymus-Expressed Chemokine (TECK), Interleukin -6 (IL.6), Cutaneous T-cell-attracting chemokine (CTACK), stromal cell-derived factor 1a/b (SDF.1a.B), and chemokine (C-C motif) ligand 1 (1.309).

2. The method of claim 1, wherein said biomarker signature further comprises Growth-regulated protein beta (Gro.B).

3. The method of claim 1, wherein said biomarker signature further comprises SLAM-associated protein (SAP).

4. The method of claim 1, wherein said biomarker signature further comprises fibrinogen.

5. The method of claim 1, wherein said biomarker signature further comprises Beta-nerve growth factor (B.NGF).

6. The method of claim 1, further comprising the step of determining an output value biomarker signature score, wherein said score is derived using a statistical algorithm or algorithms to produce an output value score, the score being indicative of the probability the subject has Lyme disease.

7. The method of claim 6, wherein said statistical algorithm or algorithm employs a logistic regression among a combination of four to twelve biomarkers.

8. The method of claim 1, further comprising the step of treating said subject with an antibiotic if said biomarker signature indicates a Lyme disease positive sample.

9. A method a treating a subject, comprising: a) having a sample from a subject tested for a biomarker signature comprising Monocyte Chemoattractant Protein 3 (MCP.3), Thymus-Expressed Chemokine (TECK), Interleukin -6 (IL.6), Cutaneous T- cell-attracting chemokine (CTACK), stromal cell-derived factor 1a/b (SDF.1a.B), and chemokine (C-C motif) ligand 1 (1.309); b) determining a Lyme disease risk score from said biomarker signature; and c) treating said subject with an antibiotic if said risk score indicates a likelihood of Lyme disease.

10. The method of claim 9, wherein said biomarker signature further comprises Growth-regulated protein beta (Gro.B).

11. The method of claim 9, wherein said biomarker signature further comprises SLAM-associated protein (SAP).

12. The method of claim 9, wherein said biomarker signature further comprises fibrinogen.

13. The method of claim 9, wherein said biomarker signature further comprises Beta-nerve growth factor (B.NGF).

14. The method of claim 9, wherein said determining a Lyme disease risk score comprises using a statistical algorithm or algorithms to produce an output value score, the score being indicative of the probability the subject has Lyme disease.

15. The method of claim 14, wherein said statistical algorithm or algorithm employs a logistic regression among a combination of four to twelve biomarkers.

* * * * *